United States Patent [19]

Capai et al.

[11] Patent Number: 5,175,358

[45] Date of Patent: Dec. 29, 1992

[54] PREPARATION OF LAEVULINIC ACID

[75] Inventors: Bernard Capai, Viarmes; Guy Lartigau, Savigny Sur Orge, both of France

[73] Assignee: Societe Francaise D'Organo-Synthese, Courbevoie, France

[21] Appl. No.: 448,299

[22] Filed: Dec. 11, 1989

[30] Foreign Application Priority Data

Dec. 9, 1988 [FR] France .................................. 88 16509

[51] Int. Cl.⁵ .............................................. C07C 51/16
[52] U.S. Cl. ..................................... 562/537; 562/577
[58] Field of Search ................................ 562/537, 577

[56] References Cited

U.S. PATENT DOCUMENTS 2,738,367  3/1956  Redmon ............................. 562/577
3,752,849  8/1973  Otsuka et al. ....................... 562/537

FOREIGN PATENT DOCUMENTS 685143  12/1939  Fed. Rep. of Germany .

OTHER PUBLICATIONS

Patent Abstracts of Japan, vol. 12, No. 132 (C-490) [2979], Apr. 22, 1988; JP-A-62 252 742 (Ube Ind. Ltd) Apr. 11, 1987.

*Primary Examiner*—Arthur C. Prescott
*Attorney, Agent, or Firm*—Burns, Doane, Swecker & Mathis

[57]  ABSTRACT

Essentially pure and colorless laevulinic acid is produced by heating and ring-opening furfuryl alcohol in the presence of water and a strong non-oxidizing protonic acid, and which includes establishing a reaction medium containing water, the strong protonic acid and a reaction solvent amount of laevulinic acid, and progressively introducing the furfuryl alcohol into such reaction medium.

16 Claims, No Drawings

PREPARATION OF LAEVULINIC ACID

BACKGROUND OF THE INVENTION

1. Field of the Invention

The present invention relates to the preparation of laevulinic acid and, more especially, to the preparation of laevulinic acid from furfuryl alcohol.

2. Description of the Prior Art

Laevulinic acid or 4-oxopentanoic acid is a known intermediate for the synthesis of pharmaceuticals and other chemical compounds.

It is prepared via two different routes:

It can be prepared by heating sugars such as glucose, sucrose, molasses or starch in dilute hydrochloric acid. This preparation does not afford high yields and can hardly be used industrially.

Laevulinic acid can also be prepared by opening the ring of furfuryl alcohol in water and in the presence of an oil. Thus, U.S. Pat. No. 3,752,849 describes such a process using a water-soluble ketone as the reaction solvent. Such a process provides good yields However, the ketone used as the solvent itself intervenes in secondary aldolization and condensation reactions. By this process, a colored laevulinic acid is obtained, even after distillation, and the content of laevulinic acid does not exceed 98% because of the great difficulties in separating its impurities therefrom.

SUMMARY OF THE INVENTION

Accordingly, a major object of the present invention is the provision of a novel, far simpler improved process for the preparation of laevulinic acid from furfuryl alcohol, which improved process conspicuously ameliorates the disadvantages of the prior art processes and which provides essentially colorless laevulinic acid in a purity of greater than 98% by simple distillation.

Briefly, the present invention features a process for the preparation of laevulinic acid by heating furfuryl alcohol in the presence of water and a strong protonic acid which is not oxidizing under the operating conditions of the reaction, and wherein the furfuryl alcohol is progressively introduced into a mixture of water, the strong protonic acid and an amount of laevulinic acid which serves as the reaction solvent.

DETAILED DESCRIPTION OF THE PREFERRED EMBODIMENTS OF THE INVENTION

More particularly according to the present invention, by the term "strong protonic acid" is intended a protonic acid having an acidity function Ho of not more than −4.

Exemplary of such strong protonic acids are the hydrohalic acids, such as hydrochloric acid, hydrobromic acid and hydriodic acid; sulfuric acid, pyrosulfuric acid, perchloric acid, the phenylsulfonic acids, methanesulfonic acid, trifluoromethanesulfonic acid, chlorosulfonic acid and fluorosulfonic acid.

The hydrohalic acids which exhibit no oxidizing activity are the preferred.

In practice, hydrochloric acid, which is very suitable and is cheap, will typically be used.

The amount of water used can vary over very wide limits.

Normally, from 1 mole to 25 moles of water are used per 1 mole of furfuryl alcohol, and preferably from 1.5 moles to 10 moles of water per 1 mole of furfuryl alcohol.

The amount of laevulinic acid employed in the reaction as a solvent can also vary over wide limits In general, an amount of laevulinic acid representing, by weight with respect to the total weight of furfuryl alcohol used in the reaction, from 30% to 1,000%, and preferably from 50% to 500%, will be introduced.

The amount of strong protonic acid employed is such that it represents from 1% to 50% with respect to the total weight of water used, and preferably from 2% to 20%.

The temperature at which the process according to the invention is carried out is preferably not less than 60° C.

The upper limit is essentially influenced by the boiling point of the different constituents of the reaction mixture and the pressure at which the reaction is carried out.

At atmospheric pressure, the upper temperature limit is advantageously 100° C. If the reaction is carried out in a closed container under the autogenous pressure of the constituents of the reaction mixture, the upper limit will be 250° C.

The furfuryl alcohol is progressively introduced by pouring, by injection or by any other means, into the reactor containing the laevulinic acid, the water and the strong protonic acid.

The duration of this introduction can vary from a few minutes to several tens of hours, as a function, in particular, of the ratios of the reagents and the stirring.

Generally, the duration of introduction is from 1 hour to 12 hours; these representative values, however, are not critical.

The treatment of the final reaction mixture and the separation of the laevulinic acid are very simplified in the present process. It is sufficient, upon completion of the reaction, to remove the excess water and the strong protonic acid by distillation under reduced pressure when the protonic acid has a sufficiently low boiling point, as is the case with hydrochloric acid, hydrobromic acid and hydriodic acid.

If the strong protonic acid is not volatile, it will first be necessary to neutralize it, for example using an alkali metal hydroxide or an alkali metal carbonate, then to separate the salt formed by any known method.

The amount of laevulinic acid is determined, for example by potentiometry, in the crude mixture.

Separation of the laevulinic acid from the byproducts which can form during the reaction and which are, in particular, compounds of a polymeric nature formed by condensation of furfuryl alcohol with itself, is carried out by distillation under reduced pressure.

The present process permits a laevulinic acid of high purity and having no color, or a very slight very pale yellow color, to be produced. The absence of a third solvent avoids the formation of various by-products resulting from secondary reactions involving the said third solvent. These by-products are generally highly colored, in particular those which result from the use of a ketone as the solvent, and are generally very difficult to separate from the laevulinic acid.

In order to further illustrate the present invention and the advantages thereof, the following specific examples are given, it being understood that same are intended only as illustrative and in nowise limitative.

EXAMPLE 1

The following materials were charged into a 6-liter glass reactor provided with a stirrer, a dropping funnel and a thermometer:
(i) 2,550 g of laevulinic acid (98%);
(ii) 990 g of water;
(iii) 150 g of a 37% by weight aqueous solution of hydrochloric acid.

The reaction mixture was stirred and heated to 90° C.

Maintaining the temperature at 90° C., 2,940 g (30 moles) of furfuryl alcohol was poured into the reactor over 6 hours.

Upon completion of the pouring, the excess water and the hydrochloric acid were distilled off under reduced pressure.

5,841 g of a fluid brown oil were obtained which contained (measured by potentiometry) 92.4% of laevulinic acid (that is, after deduction of the initial laevulinic acid, a yield of laevulinic acid formed, but not isolated, of 83.3% with respect to the furfuryl alcohol introduced).

The crude laevulinic acid was rectified under reduced pressure (670 Pa); the following were obtained:
(a) temperature of the laevulinic acid vapors at 670 Pa : from 122° C. to 124° C.;
(b) color of the distilled laevulinic acid (according to the Gardner color scale : 1 to 2, namely, from colorless to very pale yellow);
(c) weight of the distilled laevulnic acid : 5,455 g;
(d) purity of the distilled laevulinic acid : 98.8%;
(e) yield (after deduction of the laevulinic acid engaged as solvent) of laevulinic acid isolated with respect to the furfuryl alcohol introduced : 83.0%.

COMPARATIVE EXPERIMENT A

The following materials were charged into a 6-liter glass reactor provided with a stirrer, a dropping funnel and a thermometer:
(i) 2,160 g of methyl ethyl ketone;
(ii) 252 g of water;
(iii) 252 g of a 37% by weight aqueous solution of hydrochloric acid.

The reaction mixture was stirred and heated under reflux (80° C.).

Maintaining the temperature at 80° C., 1,646 g (16.8 moles) of furfuryl alcohol were poured into the reactor over 6 hours.

Upon completion of the pouring, the methyl ethyl ketone, the excess water and the hydrochloric acid were distilled off under reduced pressure.

1,812 g of a fluid brown oil were obtained which contained (measured by potentiometry) 82.0% of laevulinic acid, (namely, a yield of laevulinic acid formed, but not isolated, of 76.2% with respect to the furfuryl alcohol introduced).

The crude laevulinic acid was rectified under reduced pressure (670 Pa); the following were obtained:
(a) temperature of the laevulinic acid vapors under 670 Pa : from 123° C. to 125° C.;
(b) color of the distilled laevulinic acid (according to the Gardner color scale : from 3 to 4, namely, yellow);
(c) weight of the distilled laevulinic acid : 1,530 g;
(d) purity of the distilled laevulinic acid : 97.0%;
(e) yield of laevulinic acid isolated with respect to the furfuryl alcohol introduced : 76.1%.

After redistillation, the purity of the laevulinic acid remained at 97%. The laevulinic acid remained contaminated by aldolization/crotonization products of the methyl ethyl ketone (identification by gas-liquid chromatography and by infra-red).

COMPARATIVE EXPERIMENT B

The following materials were charged into a 6-liter glass reactor provided with a stirrer, a dropping funnel and a thermometer:
(i) 1,950 g of methyl isobutyl ketone;
(ii) 680 g of water;
(iii) 441 g of a 37% by weight aqueous solution of hydrochloric acid.

The reaction mixture was stirred and heated to 80° C.

Maintaining the temperature at 80° C., a solution consisting of 294 g (3 moles) of furfuryl alcohol in 600 g of methyl isobutyl ketone was poured into the reactor over 4 hours.

Upon completion of the pouring, the methyl isobutyl ketone, the excess water and the hydrochloric acid were distilled off under reduced pressure.

328.5 g of a fluid brown oil were obtained.

The crude laevulinic acid was rectified under reduced pressure (670 Pa); the following were obtained:
(a) color of the distilled laevulinic acid (according to the Gardner color scale) : 3 to 4, namely, yellow);
(b) weight of the distilled laevulinic acid : 267 g;
(c) purity of the distilled laevulinic acid : 94.0%;
(d) yield of isolated laevulinic acid with respect to the furfuryl alcohol introduced : 72.1%.

After redistillation, the purity of the laevulinic acid remained at 94.0%. The laevulinic acid remained contaminated by aldolization/crotonization products of methyl isobutyl ketone (identification by gas-liquid chromatography and by infra-red).

EXAMPLE 2

The following materials were charged into a 1-liter glass reactor provided with a stirrer, a dropping funnel and a thermometer:
(i) 255 g of laevulinic acid (98%);
(ii) 99 g of water;
(iii) 26.2 g of a 47% by weight aqueous solution of hydrobromic acid.

The reaction mixture was stirred and heated to 90° C.

Maintaining the temperature at 90° C., 294 g (3 moles) of furfuryl alcohol were poured into the reactor over 6 hours.

Upon completion of the pouring, the excess water and the hydrobromic acid were distilled off under reduced pressure.

580 g of a fluid brown oil were obtained which contained (measured by potentiometry) 88% of laevulinic acid (namely, after deduction of the initial laevulinic acid, a yield of laevulinic acid formed, but not isolated, of 73.3% with respect to the furfuryl alcohol introduced).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of laevulinic acid, including heating furfuryl alcohol in the presence of water and a strong non-oxidizing protonic acid, and comprising establishing a reaction medium containing water, said strong protonic acid and a reaction solvent amount of laevulinic acid, and progressively introducing said furfuryl alcohol into such reaction medium.

2. The process as defined by claim 1, said strong protonic acid having an acidity constant Ho of not more than −4.

3. The process as defined by claim 2, said strong protonic acid comprising hydrochloric acid, hydrobromic acid, hydriodic acid, sulfuric acid, pyrosulfuric acid, perchloric acid, a phenylsulfonic acid, methanesulfonic acid, trifluoromethanesulfonic acid, chlorosulfonic acid or fluorosulfonic acid.

4. The process as defined by claim 3, said strong protonic acid comprising hydrochloric acid, hydrobromic acid or hydriodic acid.

5. The process as defined by claim 1, wherein the amount of water ranges from 1 mole to 25 moles thereof per 1 mole of furfuryl alcohol.

6. The process as defined by claim 1, wherein the amount of laevulinic acid, expressed by weight relative to the total weight of furfuryl alcohol used in the reaction, ranges from 30% to 1,000%.

7. The process as defined by claim 1, wherein the amount of strong protonic acid ranges from 1% to 50% by weight relative to the total weight of water employed.

8. The process as defined by claim 1, carried out at a temperature of not less than 60° C.

9. The process as defined by claim 8, carried out under atmospheric pressure at a temperature ranging from 60° C. to 100° C.

10. The process as defined by claim 8, carried out under the autogenous pressure of the constituents of the reaction mixture, at a temperature ranging from 60° C. to 250° C.

11. The process as defined by claim 1, comprising progressively introducing said furfuryl alcohol into said reaction medium over a period of time ranging from a few minutes to several tens of hours.

12. The process as defined by claim 4, said strong protonic acid comprising hydrochloric acid.

13. The process as defined by claim 5, said amount of water ranging from 1.5 moles to 10 moles per 1 mole of furfuryl alcohol.

14. The process as defined by claim 6, said amount of laevulinic acid ranging from 50% to 500%.

15. The process as defined by claim 7, said amount of strong protonic acid ranging from 2% to 20%.

16. The process as defined by claim 11, carried out for from 1 hour to 12 hours.

* * * * *